(12) United States Patent
Al-Oboudi (10) Patent No.: US 8,221,341 B1
(45) Date of Patent: Jul. 17, 2012

(54) ADJUSTABLE RESPONSE ANKLE FOOT ORTHOTIC

(76) Inventor: Waleed Al-Oboudi, La Jolla, CA (US)

( * ) Notice: Subject to any disclaimer, the term of this patent is extended or adjusted under 35 U.S.C. 154(b) by 0 days.

(21) Appl. No.: 11/685,126

(22) Filed: Mar. 12, 2007

Related U.S. Application Data (60) Provisional application No. 60/781,066, filed on Mar. 10, 2006.

(51) Int. Cl.
*A61F 5/00* (2006.01)
(52) U.S. Cl. .................. 602/27; 602/23; 602/65; 36/31; 36/103
(58) Field of Classification Search .............. 602/16, 602/23, 66, 12, 27–29, 65; 36/102, 103, 36/31
See application file for complete search history.

(56) References Cited

U.S. PATENT DOCUMENTS

| | | | | |
|---|---|---|---|---|
| 2,352,532 A * | 6/1944 | Ghez et al. | .......................... | 36/33 |
| 4,309,832 A * | 1/1982 | Hunt | ............................. | 36/32 R |
| 5,370,133 A * | 12/1994 | Darby et al. | ................... | 128/882 |
| 5,460,600 A * | 10/1995 | Bieling | ............................. | 602/27 |
| 5,486,157 A * | 1/1996 | DiBenedetto | .................... | 602/27 |
| 5,571,078 A * | 11/1996 | Malewicz | ......................... | 602/27 |
| 6,056,712 A * | 5/2000 | Grim | ................................ | 602/27 |
| 6,267,742 B1* | 7/2001 | Krivosha et al. | ................ | 602/28 |
| 6,602,215 B1* | 8/2003 | Richie, Jr. | ......................... | 602/27 |
| 2002/0188238 A1* | 12/2002 | Townsend et al. | ............... | 602/26 |

* cited by examiner

*Primary Examiner* — Patricia Bianco
*Assistant Examiner* — Keri J Nelson
(74) *Attorney, Agent, or Firm* — Knobbe, Martens, Olson & Bear, LLP (57) ABSTRACT

An ankle-foot orthotic device incorporating an adjustable response system allowing the hindfoot to recognize that the foot landed on the heel during a walking sequence is provided. The device is constructed to provide feedback for the patient to make adjustments needed throughout the body structures to prepare for weight transfer onto the foot during gait. The system also helps the patient to maintain toe extension during a walking sequence. The device generally incorporates an articulated foot support and a foot support insert configured to substantially inhibit supination or pronation of the mid foot.

7 Claims, 7 Drawing Sheets

ADJUSTABLE RESPONSE ANKLE FOOT ORTHOTIC

CROSS-REFERENCE TO RELATED APPLICATIONS

This application claims the benefit of priority under 35 U.S.C. §119(e) of U.S. Provisional Application No. 60/781,066 filed on Mar. 10, 2006, which is incorporated herein by reference in its entirety.

BACKGROUND OF THE INVENTION

1. Field of the Invention

The present invention generally relates to orthotic devices and, in particular, relates to an orthotic device for use in providing correction to the ankle and foot and the promotion of more normal alignment at rest and with movement. Certain preferred implementations of the device are designed for patients affected by a stroke or brain injury and/or those who demonstrate lack of control and/or imbalance of muscle activity in the ankle and foot.

2. Description of the Related Art

Individuals who suffer from a stroke or other neurological impairments often demonstrate imbalance of muscle activity and lack of control in the ankle and foot, which often manifests in the individual walking with various deviations. These deviations include, but are not limited to, foot inversion, plantar flexion, toe flexion, and lack of opposing movements, which may lead to contact with the floor that is not conducive to weight transfer over the foot, resulting in damage or stress on the foot and/or ankle and interference with normal gait and function.

Physical therapy is usually used to restore the patient's normal gait stride and other motor skills. As part of the treatment, medical professionals often utilize orthotic devices such as ankle-foot orthosis (AFO) in gait training exercises. An AFO is typically attached to the patient's foot to brace the foot and guide the foot to move in a proper orthopedic manner. Conventional AFO devices, however, utilize a one-piece rigid footplate which underlies the foot. When a patient fitted with a conventional AFO attempts to walk, the one-piece, rigid footplate may not provide the normal sensory experience of the pressure on the heel, which is important in eliciting a reaction throughout the limb and the rest of the body to prepare for weight transfer. In addition, the common one-piece footplate does not allow for dissociation or independent movement of different sections of the foot such as the forefoot from the mid foot and the hind foot, which permits normal function of the foot in that it allows for adjustments necessary for balance and maintaining of normal contact with the floor or other walking surface. To this end, it will be appreciated that there is a need for an improved orthosis designed to restore limb and joint function of patients and does not impede restoration of the patient's motor skills.

SUMMARY OF THE INVENTION

In one aspect, the preferred embodiments of the present invention provide an ankle-foot orthotic device incorporating an adjustable response system allowing the hindfoot to recognize that the foot landed on the heel during a walking sequence, which in turn provides feedback for the patient to make adjustments needed throughout body structures to prepare for weight transfer onto the foot during gait. The system also helps the patient to maintain toe extension during a walking sequence, which allows the patient to dorsiflex with less effort and allows the foot to transfer weight moving forward to a more natural terminal stance.

In one embodiment, the device comprises an articulated foot support, which in some implementations is in the form of a foot plate. In one version, the foot support comprises an inner portion and an outer portion. The outer portion is preferably articulated and comprises a plurality of individual segments that are independently attached to the inner portion. Preferably, each individual segment comprises a substantially rigid material that is designed to correspond to specific segment of the foot. The inner portion preferably comprises a generally flexible material that is designed to flex when the foot is engaged in a walking sequence such that the patient can bend or flex the foot along sections that are directly above a rigid segment of the outer portion. In one implementation, the device further comprises a foot support insert configured so as to substantially inhibit supination or pronation of the mid foot, adduction and abduction of the forefoot, toe flexion, and overall foot inversion and eversion. Preferably, the foot support insert comprises carbon fiber. In one embodiment, the device further comprises a calcaneal control interconnected to the joint which serves to stabilize and influence heel position so as to substantially inhibit varus and valgus movement of the calcaneous in the hind foot. Preferably, the inner sole comprises a valgus movement of the calcaneous in the hind foot. Preferably, the inner sole comprises a modified polyethylene, a copolymer, or the like. In one embodiment, the foot support is interconnected to a calf support mechanism that conforms approximately to the calf portion of the patient's leg. The foot support and calf support mechanism are preferably interconnected by a free motion ankle joint, a dorsiflexion assist, or a resist control.

DETAILED DESCRIPTION OF THE PREFERRED EMBODIMENT

Preferred embodiments of the disclosed invention provide for a new and unique adjustable response ankle and foot orthotic device which substantially inhibits misalignment and provides more normal alignment of the ankle and foot with respect to the leg. Use of the device substantially reduces ankle injuries in order to help patients effected by a stroke or brain injury to restore the normal alignment and function of the foot during walking and function in upright postures. Embodiments of the device further incorporate an articulating foot support which allows a patient using the device to flex and stretch the foot in a manner associated with a normal gait stride while also providing protective support to the foot and ankle. The device 100 generally comprises a joint 102, a foot support 104, a calf capture mechanism 106, and a plurality of adjustable securing mechanisms 110.

Figure 1:
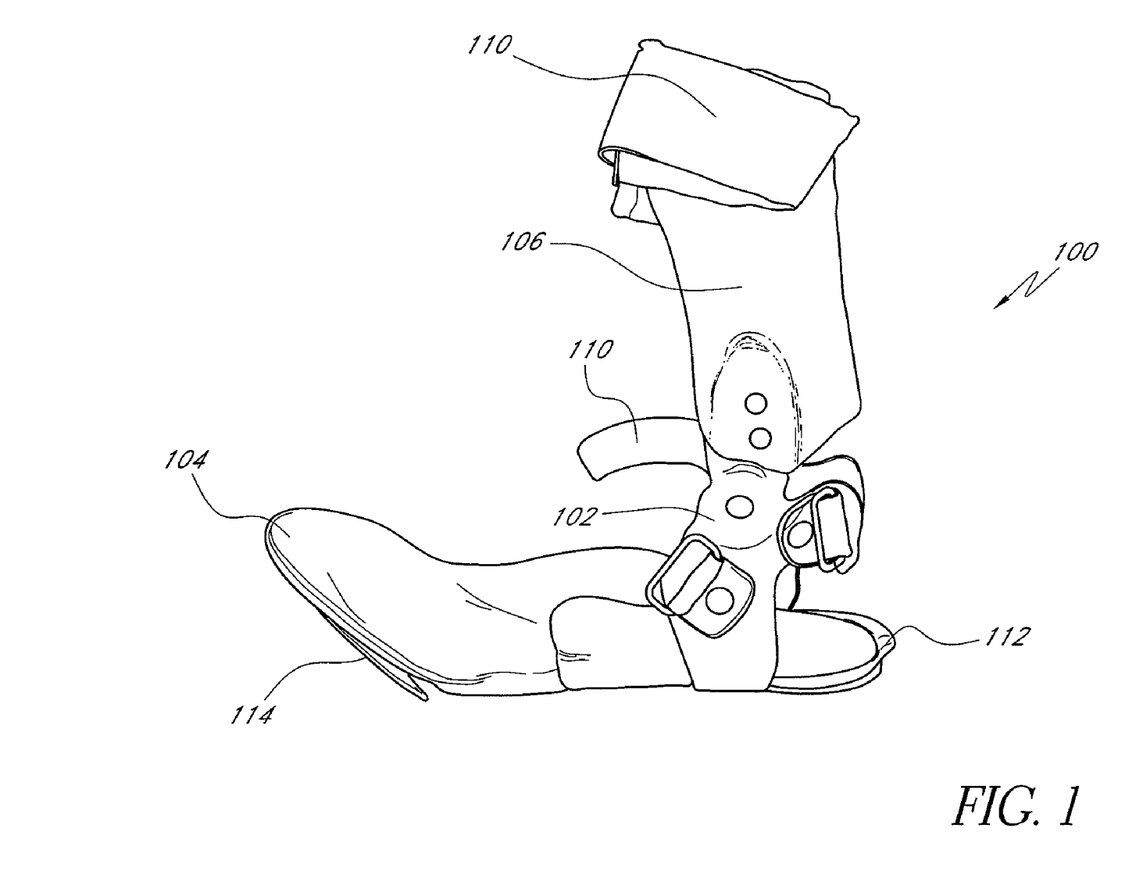
FIG. 1 is a side view of one embodiment of the ankle-foot orthotic device.
Figure 2:
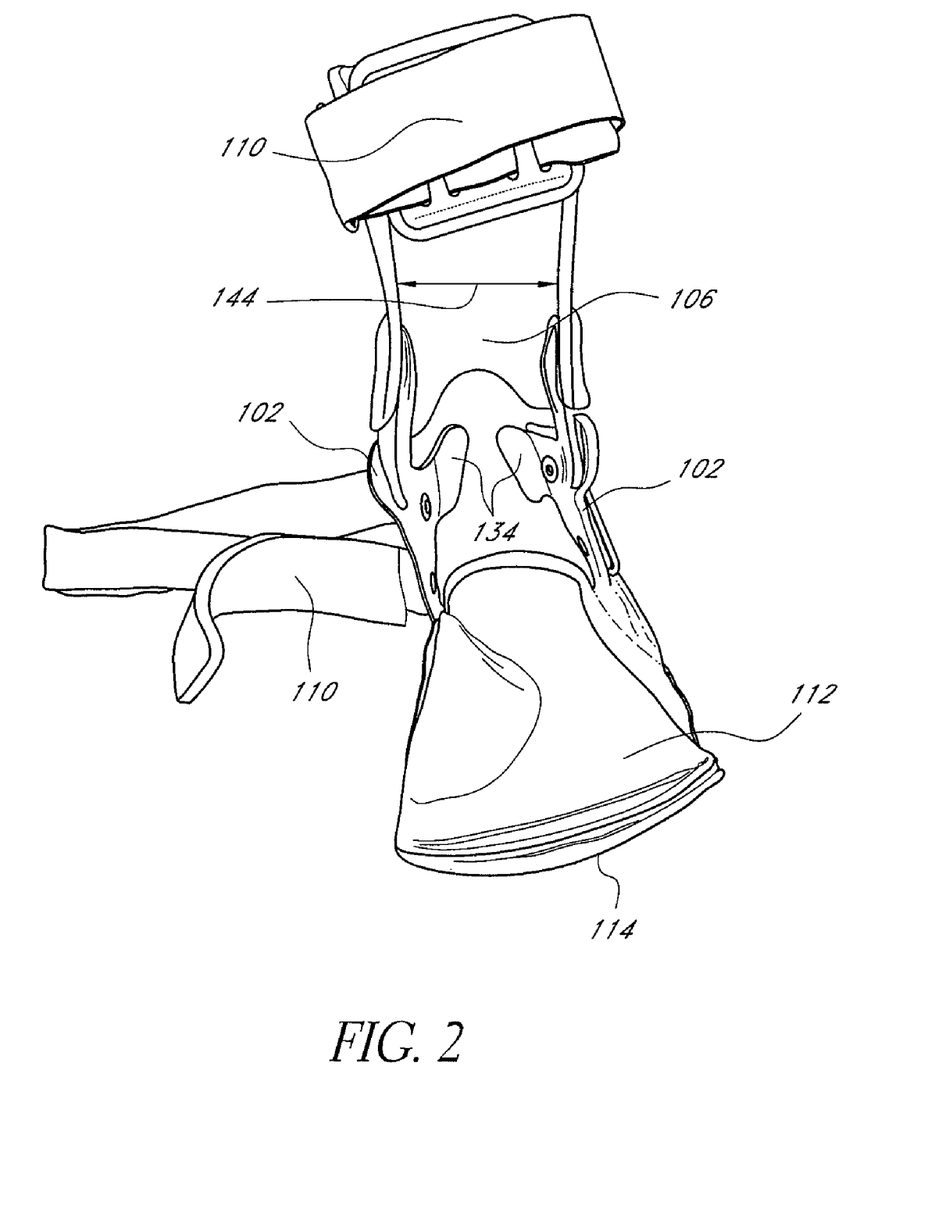
FIG. 2 is a front view of one embodiment of the ankle-foot orthotic device.

FIGS. 1-2 illustrate one embodiment of the ankle and foot orthotic device 100. The joint 102 connects the foot support 104 to the calf support mechanism 106. In general, the foot support 104 of the device 100 is configured to receive a person's foot and the calf support mechanism 106 is adapted to receive at least a portion of the person's calf. The adjustable securing mechanism 110 may be used to secure the calf and foot in place with respect to the device 100. While in the device, the foot, ankle, and leg are substantially properly aligned with respect to each other so as to prevent injury to the foot and ankle. The device also acts to inhibit undesirable lateral and rotational motion of the foot and ankle during walking, further preventing injury. The joint 102 and foot support 104 are additionally configured so to allow the device to articulate or move in a manner that allows the patient wearing the device to bend and flex their ankle and foot when walking, while maintaining an orthopedically proper alignment of the foot, as discussed in greater detail below.

Figure 3A:
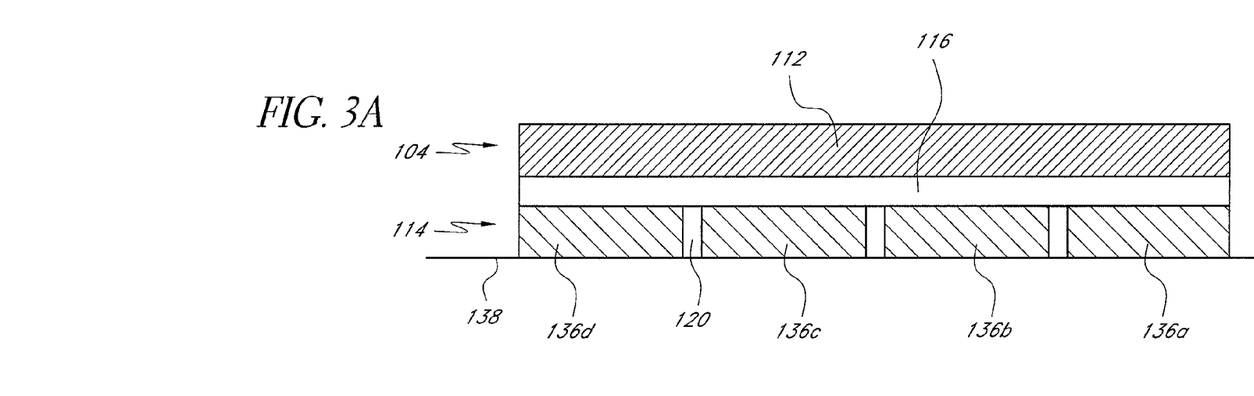
FIG. 3A is a schematic side view illustration of one embodiment of the foot support.
Figure 3B:
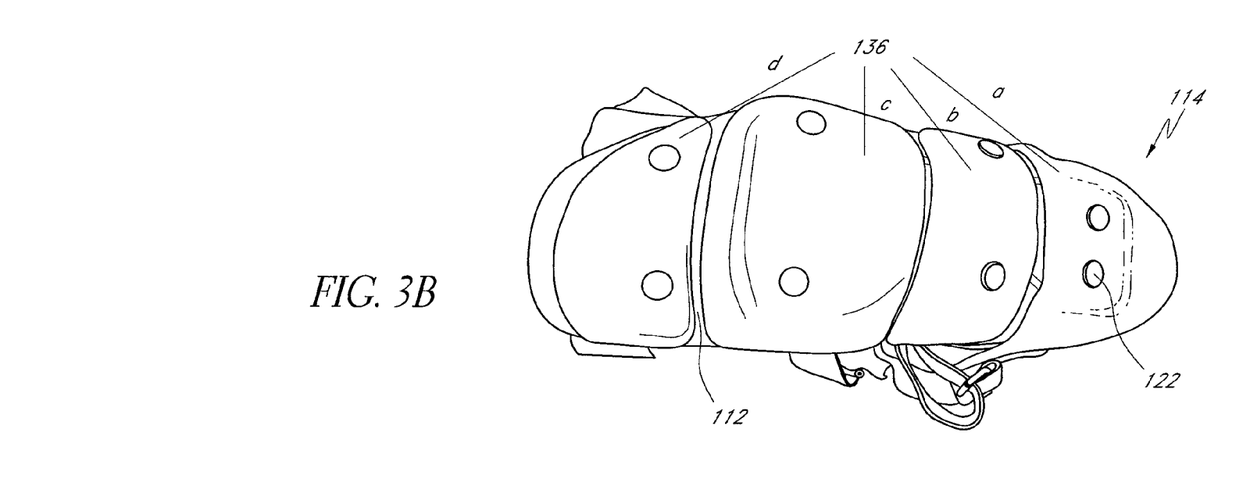
FIG. 3B is a bottom view of one embodiment of the foot support.

FIGS. 3A-B schematically illustrate side and bottom views of one embodiment of the foot support 104. The foot support 104 generally comprises an inner portion 112, an outer portion 114, and an optional insert 116. The foot support 104 is generally dimensioned in the approximate shape of the sole of a human foot so that the foot support 104 substantially spans the entire sole of the foot. In one embodiment, the inner portion 112 is positioned as an upper layer of the foot support 104, which is located adjacent to the patient's foot, while the outer portion 114 is positioned below the inner portion 112, and is configured to contact the walking surface or inside of the patient's shoe. When utilized in the device 100, the insert 116 is located between the inner portion 112 and outer portion 114 to remedy supination/pronation problems, as discussed in greater detail below with respect to the insert 116.

In one embodiment, illustrated in FIGS. 3A-B, the articulated outer portion 114 comprises a plurality of rigid segments 136a-d which preferably correspond to the sections of a person's foot: the hind foot, the mid foot, the forefoot, and the toes. The inner portion 112 comprises a single, relatively compliant sheet which substantially spans the outer portion 114. Each of the rigid segments 136a-136d is interconnected at a predetermined position to the inner portion 112. In a preferred embodiment, rivets 122 are utilized to secure the inner portion 112, outer portion 114, and insert 116 to each other, however alternative embodiments may employ other securing mechanisms generally understood by those knowledgeable in the art. Each of the rigid segments 136a-136d are positioned substantially out of contact with the other segments, forming gaps 120 between each of the segments 136a-136d, each gap 120 bridged by the inner portion 112. These gaps 120 allow each of the outer portion segments to articulate, move, and/or flex independently of the others. As discussed in greater detail below, in certain embodiments, the rigid segments 136a-d are configured so as to substantially constrain the corresponding portion of the patient's foot in proper orthopedic alignment. Further, this alignment, combined with the ability of the segments 136a-d to independently articulate or move allows substantially more normal movements and adjustments in corresponding parts of the foot.

In use, as the patient walks forward naturally, the first portion of the foot to land is the hind foot. As the hind foot segment 136a dissociates or articulates independently of the other segments 136b-d, the hind foot segment 136a also lands first. As a result, the patient's hind foot may recognize that the foot has landed on the heel during walking forward. This recognition in turn provides feedback to the patient in order to make the adjustments needed throughout structures above the foot to prepare for weight transfer onto the foot during gait.

The mid foot section 136b of the foot support corresponds to the midfoot area of the foot and is relatively dissociated from adjacent foot support sections. In one embodiment, the mid foot section 136b possesses an arch that allows for substantially partial compression of the patient's mid foot and allows the patient's foot to move closer to the floor during weight bearing, corresponding to natural movement of the foot. When the weight is taken off the foot, the mid foot section 136b moves up, shadowing natural movement of the patient's mid foot. This adjustable arch substantially prevents foot breakdown, allows for natural adjustments toward appropriate pronation during weight bearing, and returns to neutral position during non-weight bearing. This unique feature of the mid foot segment 136b allows for adjustments to be made in order to help the patient in regaining, maintaining and/or attaining the state of balance, as discussed below.

The forefoot section 136c of the foot support corresponds to the forefoot area of a person. The ability of the forefoot section 136c to dissociate or articulate independently of the other sections 136a, 136b, and 136d allows for adjustment in the forefoot with an emphasis on maintaining toe extension. Toe extension is important for normal gait, as it allows the foot to transfer weight moving forward to a more natural terminal stance where the toes are naturally extended. Toe extension also allows the patient to contact the floor at the metatarsal heads when walking backwards. Toe extension further allows the patient to dorsiflex with less effort, as the patient will not be fighting the forces of toe flexion which is common with patients effected with stroke or brain injury. The forefoot section 136c is also designed so as to extend the toes in the natural curve that shadows normal anatomy of the foot.

The independent articulation of the sections 136a-d also allows the patient to perform additional functions of the foot safely while wearing the device. A series of adjustments in the equilibrium reactions of the foot takes place in the mid foot and forefoot when balancing. Similarly, necessary movements of the foot towards eversion and inversion are accomplished by a combination of movements in the mid foot and forefoot. By allowing independent articulation of the fore foot segment 136c and the mid foot segment 136b, the patient's foot may make movement adjustments for balance or eversion/inversion, as necessary. Further, in the process of making these movements, the rigid hind foot segment 136a stabilizes the patient's hind foot, thus substantially preventing injury in the ankle.

In certain embodiments, the outer portion 114 is fabricated of a co-polymer, while the inner portion 112 is fabricated of a modified polyethylene. Advantageously, as the underside of the outer portion 114 is intended to contact walking surfaces or the interior of the patient's shoe, construction of the outer portion 114 from a hard, wear resistant material enhances the wear resistance of the outer portion 114 while urging the feet into proper alignment while walking. Additionally, while certain preferred embodiments of the device provide for four segments 136, alternative embodiments may provide for fewer or greater than four segments, as necessary.

In one embodiment, the foot support insert 116 may comprise a carbon fiber insert. The carbon fiber insert is comprised of a plurality of laminated sheets, which are cut to size, heated, and formed to the predetermined shape necessitated by the patient's orthopedic condition. After heating, the fiber sheets re-laminate themselves. The insert 116 is subsequently placed into proper position between the inner and outer portions 112 and 114.

Figure 4:
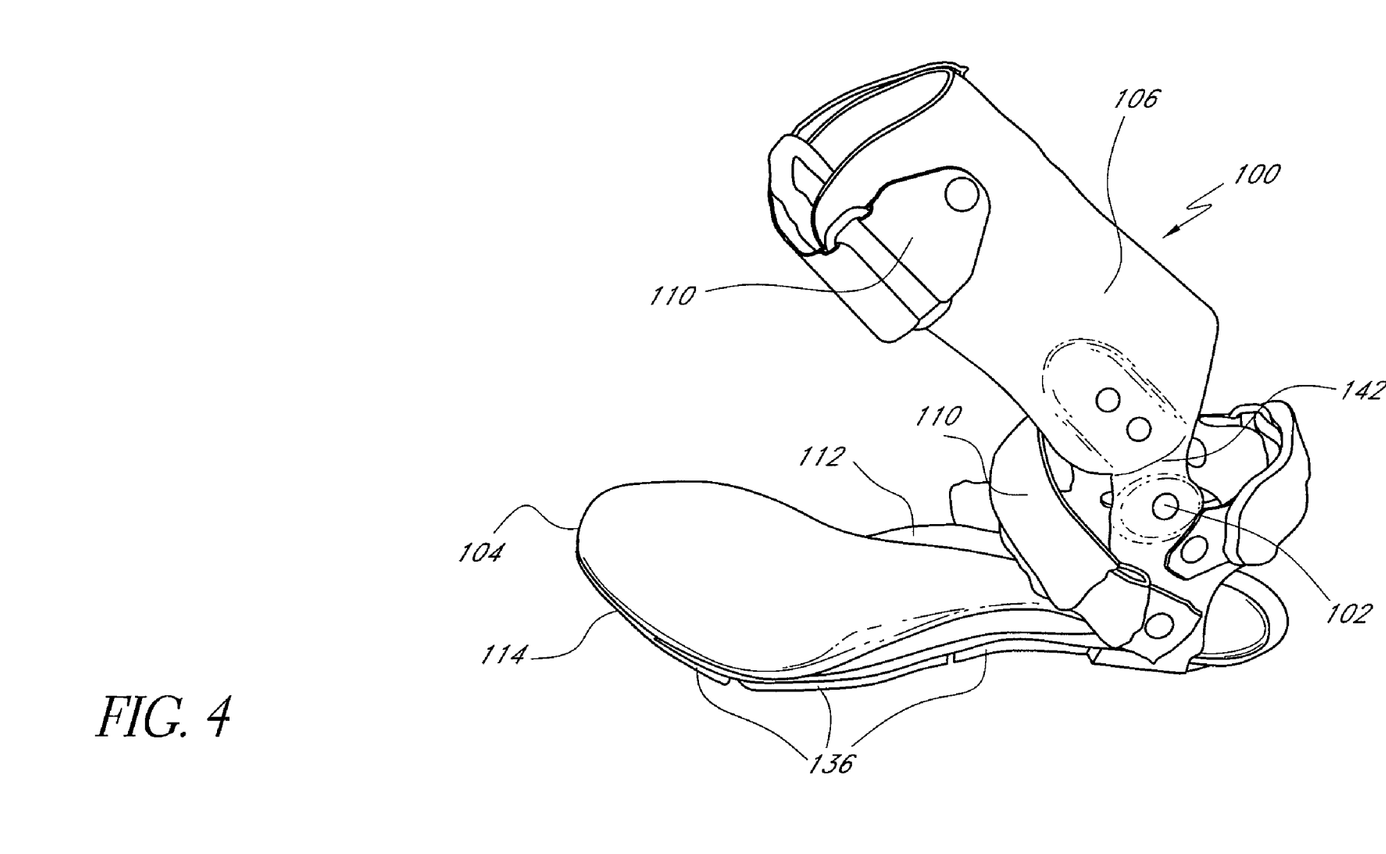
FIG. 4 is a side view of one embodiment of the ankle-foot orthotic, illustrating the capability of the orthotic to pivot at the joint.

One embodiment of the joint 102 is illustrated in FIG. 4. In general, the joint 102 is designed to work with the foot support 104 and the calf support mechanism 106 to allow a patient to bend and flex the foot in a manner substantially similar to that associated with normal gait when using the orthopedic device 100. In certain embodiments, the joint 102 is configured to allow free ankle motion, while in alternative embodiments, the joint 102 is configured to provide a patient dorsiflexion assist.

In one embodiment, the joint 102 is positioned approximately at the ankle of the patient. There, when the patient moves his ankle, the orthotic device 100 will pivot as well. In conjunction with the segmented outer portion 114, this joint 102 allows the patient to comfortably walk while using the orthotic device 100. Soft pads may further be placed on the interior surface of the joint arm 142, adjacent to the patient's skin, in order to provide a soft surface with which the joint arm 142 contacts the patient to enhance a patient's comfort. In certain embodiments, as illustrated in FIG. 4, the at least one securing mechanism 110 may also be mounted to the joint 102 to secure the patient's foot to the device.

Figure 5:
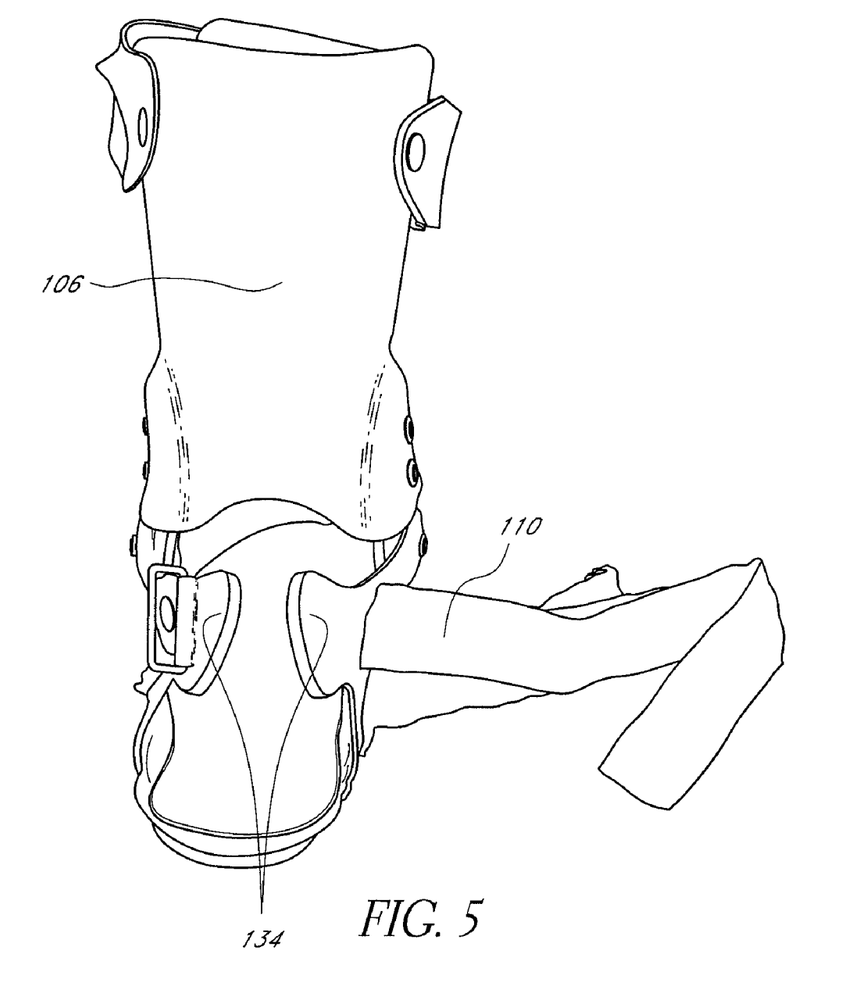
FIG. 5 is a rear view of one embodiment of the ankle-foot orthotic, illustrating two padded portions which help to align the hind foot in a neutral position.

In one embodiment, a calcaneal control device 134, which can be in the form of two padded portions as illustrated in FIG. 5, extends rearward from the joint 102 to substantially limit movement of the top of the calcaneous and to help align the hind foot in a neutral position. The calcaneal control device 134 may be secured against the top of the calcaneous by the securing mechanism 110 to enhance proper alignment.

Figure 6:
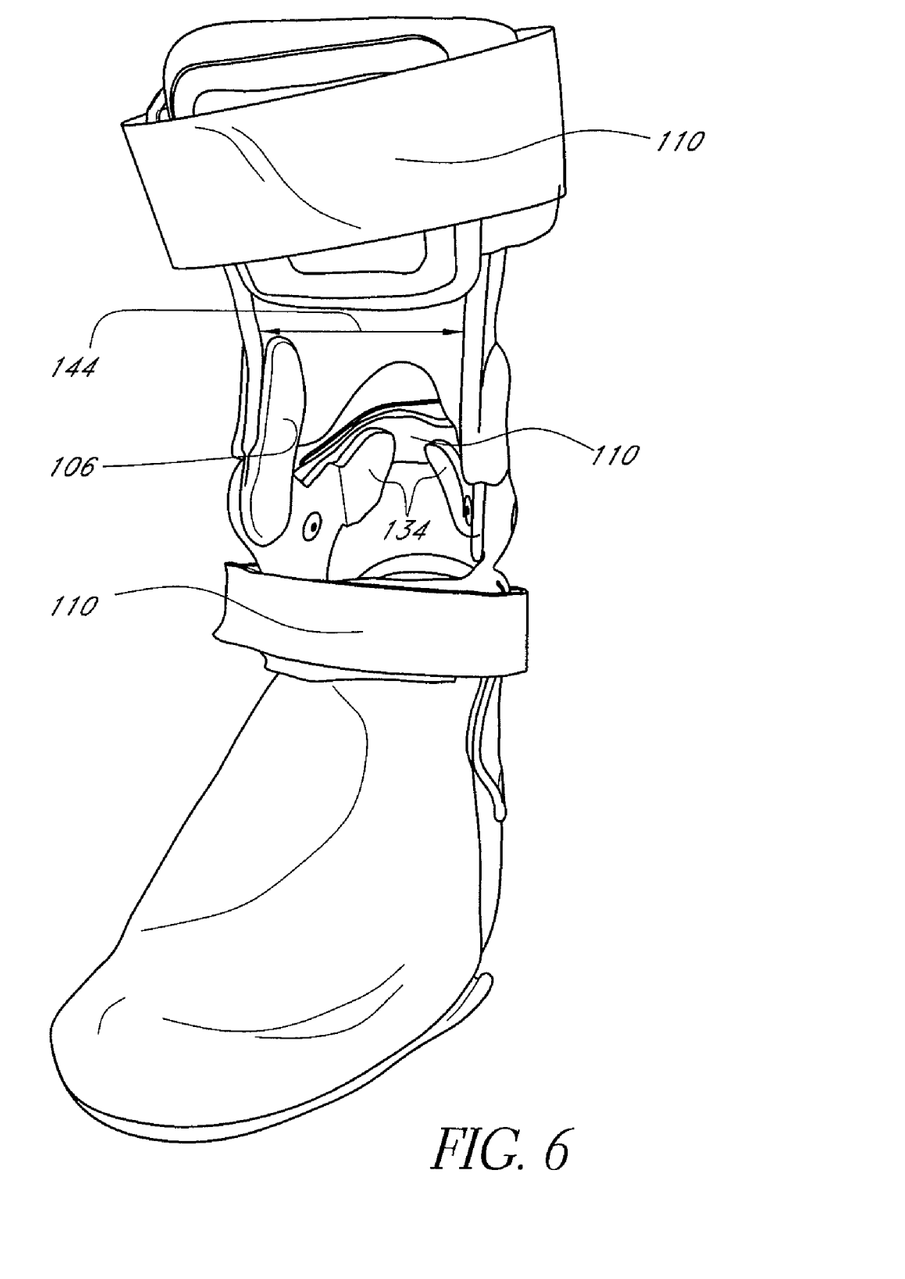
FIG. 6 is a front view of one embodiment of the ankle-foot orthotic, illustrating the calf capture mechanism.

The calf support mechanism 106 is illustrated in FIG. 6. The calf capture mechanism 106 is designed to receive at least a portion of the patient's calf so as to properly align the foot and ankle inserted in the device 100 with the leg. In this manner, friction caused by direct contact on the ankle and Achilles tendon is reduced compared to other orthotic devices. In one embodiment, the calf support mechanism 106 comprises a generally U-shaped tube containing a mouth 144. The calf capture mechanism 106 is dimensioned so as to allow a patient's calf to be inserted within.

Figure 7:
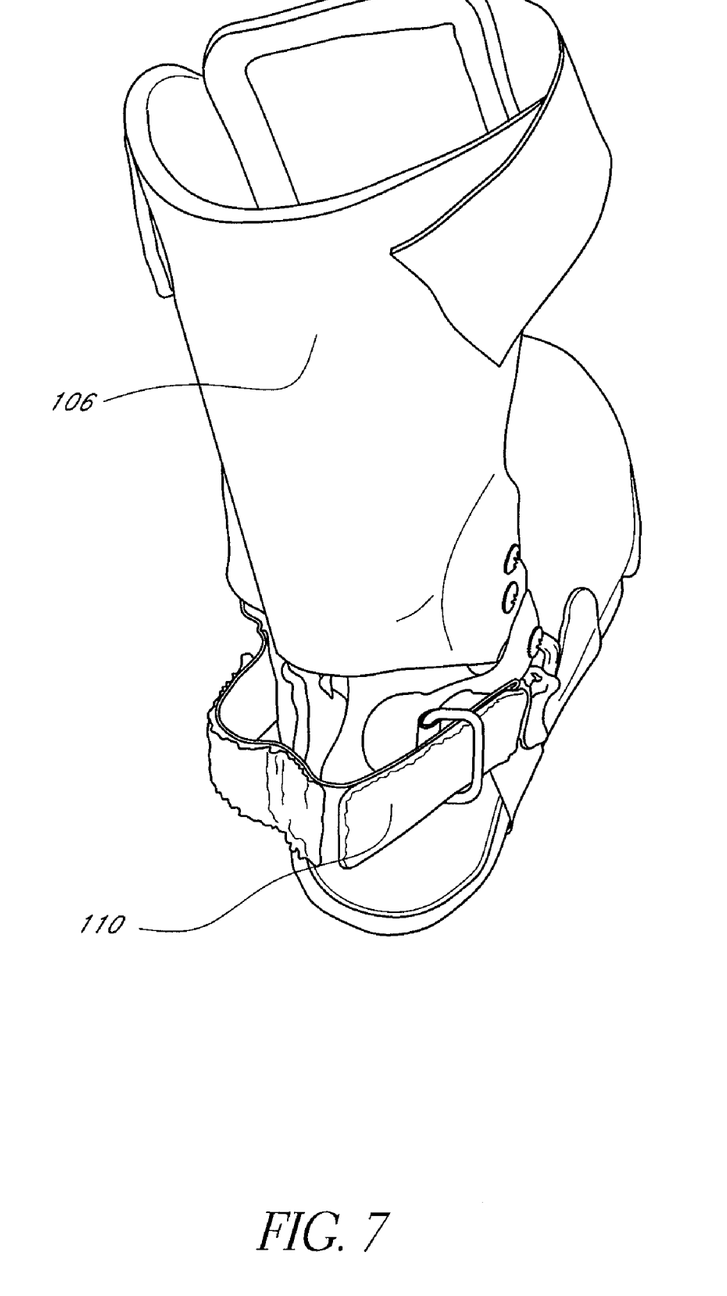
FIG. 7 is a rear view of one embodiment of the ankle-foot orthotic, illustrating the securing mechanism.

In the embodiment of FIGS. 6-7, the securing mechanism 110 comprises three straps. In alternative embodiments, fewer or greater straps may also be utilized, as necessary. The three straps are placed within the device 100 at the top of the calf capture mechanism 106, across the front of the ankle, and on both sides of the calcaneous at approximately the joint 102. The straps may be adjusted in length to secure the device 100 comfortably against the patient and allow the device to inhibit improper orientation of the foot and ankle. Additionally, soft pads may be affixed to surfaces of the securing mechanism 110 which contact the patient's skin in order to enhance patient comfort.

In another embodiment, an adjustable response system is incorporated in an ankle foot orthosis. The adjustable response system generally comprises a plurality of segments which correspond to different sections of the foot and, in some embodiments, are positioned adjacent to the patient's sole. Each segment is preferably pivotable and, in some embodiments, substantially dissociates from adjacent segments during various parts of a walking sequence. In one embodiment, the segment which corresponds to the hind foot area pivots relative to the other segments as the foot lands on the heel during a walking sequence which allows the hindfoot to recognize that the foot landed on the heel, which in turn will provide feedback for the patient to make adjustments needed to prepare for weight transfer onto the foot. In another embodiment, the segment which corresponds to the forefoot area allows for adjustment in the forefoot and maintains toe extension during a walking sequence. Preferably, the segments can dissociate and move independently which allows for mobility in the forefoot and midfoot while stabilizing the hindfoot.

Although the foregoing description has shown, described, and pointed out the fundamental novel features of the present teachings, it will be understood that various omissions, substitutions, and changes in the form of the detail of the apparatus as illustrated, as well as the uses thereof, may be made by those skilled in the art, without departing from the scope of the present teachings. Consequently, the scope of the present teachings should not be limited to the foregoing discussion, but should be defined by the appended claims.

What is claimed is:

1. An ankle-foot orthotic device, comprising:
   a foot support having an inner portion and an outer portion, wherein the outer portion has an articulated exterior surface, said articulated exterior surface comprises a plurality of distinct segments that are independently attached to the inner portion and adapted to be positioned adjacent the sole of a persons' foot, wherein each distinct segment is pivotable relative to the other segments in a manner such that each segment can dissociate from the other segments and flex independently when the person's foot engages in a walking sequence;
   a free motion ankle joint, where the ankle joint and the foot support are configured to allow the device to articulate in a manner that allows the person wearing the device to bend and flex the ankle and foot when walking while maintaining an orthopedically proper alignment of the foot; and
   a calcaneal control device adapted to stabilize the heel position so as to substantially inhibit varus and valgus movement.

2. The ankle-foot orthotic device of claim 1, wherein each of the segments on the articulated exterior surface of the foot support are separated from adjacent segments by a gap.

3. The ankle-foot orthotic device of claim 1, wherein the segments on the articulated exterior surface of the foot support comprise a toe segment, a forefoot segment, a mid foot segment, and a hind foot segment, which correspond to the person's toes, forefoot, mid foot, and hind foot respectively.

4. The ankle-foot orthotic device of claim 1, wherein the inner portion of the foot support comprises a flexible material.

5. The ankle-foot orthotic device of claim 1, wherein the calcaneal control device comprises two padded portions.

6. The ankle-foot orthotic device of claim 1, further comprising a foot support insert configured to substantially inhibit supination or pronation of the mid foot.

7. An ankle-foot orthotic device, comprising:
   a foot support adapted to be positioned against and span the entire sole of a person's foot, said foot support having an exterior surface comprising a plurality of individual distinct segments, wherein the individual segments comprise a forefoot segment, a mid foot segment, and a hindfoot segment, said segments are pivotable relative to each other;
   a calf support adapted to receive at least a portion of the person's calf; and
   a joint interconnecting the foot support and the calf support, wherein the joint is configured to provide a patient dorsiflexion assist.

* * * * *